United States Patent [19]

Wehrmann

[11] Patent Number: 5,728,707
[45] Date of Patent: Mar. 17, 1998

[54] TREATMENT AND PREVENTION OF PRIMARY AND METASTATIC NEOPLASMS WITH SALTS OF AMINOIMIDAZOLE CARBOXAMIDE

[75] Inventor: Felix Wehrmann, Wiener Neudorf, Austria

[73] Assignee: Constantia Gruppe, Austria

[21] Appl. No.: 505,439

[22] Filed: Jul. 21, 1995

[51] Int. Cl.[6] .................... A61K 31/415; A61K 31/505
[52] U.S. Cl. .................... 514/274; 424/85.4; 424/85.7; 514/2; 514/21; 514/386
[58] Field of Search .................... 514/2, 21, 274, 514/386; 424/85.4, 85.7

[56] References Cited

PUBLICATIONS

Al–Safi, S.A., and Maddocks, J.L., 1984, "Azathioprine and 6–mercaptopurine (6–MP) suppress the human mixed lymphocyte reaction (MLR) by different mechanisms", *Br. J. Clin. Pharmac.* 17:417–422.
Bonadonna, G., and Valagussa, P., 1988, "Adjuvant chemotherapy for breast cancer", *Semin. Surg. Oncol.* 4:250–255.
DeVita, V.T., et al., 1975, "Combination versus single agent chemotherapy: A review of the basis for selection of drug treatment of cancer", *Cancer* 35:98–110.
Frei, III, E., 1972, "Combination cancer therapy: Presidential address", *Cancer Res.* 32:2593–2607.
Hakala et al., 1964, "Prevention of the growth–inhibitory effect of 6–mercaptopurine by 4–aminoimidazole–5–carboxamide" *Biochim Biophys Acta* 80:665–668.
Hano, K., and Akashi, A., 1964, "Influences of anticancer agents on the metabolism of ε–aminolevulinic acid in normal and tumor–bearing mice", *Gann* 55:25–40.
Harris, C.C., 1979, "A delayed complication of cancer therapy—cancer", *J. Natl. Cancer Inst.* 63:275–277.
Horrobin, D.F., et al., 1978, "Thromboxane A2: A key regulator of prostaglandin biosynthesis and of interactions between prostaglandins, calcium and cyclic nucleotides", *Med. Hypothesis* 4:178–186.

Karmali, R.A., 1983, "Prostaglandins and cancer", *CA Cancer J Clin.* 33:322–332.
Karmali, R.A., et al., 1993, "Plant and marine n–3 fatty acids inhibit experimental metastasis of rat mammary adenocarcinoma cells", *Prost. Leuk. Essential & Fatty Acids* 48:309–314.
Myers, C.E., 1992, "Anthracyclines", *Cancer Chemother. Biol. Response Modif.* 13:45–52.
Rutty, C.J., et al., 1984, "The species dependent pharmacokinetics of DTIC", *Br. J. Cancer* 48:140.
Shealy, Y.F., and Kranth, C.A., 1966, "Imidazoles. II. 5(or 4)–(monosubstituted trizeno)imidazole–4(or 5)–carboxamides", *J. Med. Chem.* 9:34–38.
Shealy, Y.F., et al., 1962, "Imidazoles. I. Coupling reactions of 5–diazoimidazole–4–carboxamide", *J. Org. Chem.* 27:2150–2154.
Shealy, Y.F., et al., 1961, "Synthesis of potential anticancer agents. XXIX. 5–Diazoimidazole–4–carboxamide and 5–Diazo–v–triazole–4–carboxamide" *J. Org. Chem.* 26:2396–2401.
Shealy, Y.F., et al., 1962, "Antitumor activity of triazenoimidazoles", *Biochem. Pharmacol.* 11:674–676.
Terao, S., et al., 1985, "Thromboxane synthetase inhibitors: Design and synthesis of a novel series of ω–pyridylalkenoic acid", *Advances in Prostagl. Thromb. Leuk Res.* 15:315–317.
Weiss, R.B., and DeVita, Jr., V.T., 1979, "Multimodal primary cancer treatment (Adjuvant chemotherapy): Current results and future prospects", *Ann. Intern. Med.* 91:251–260.

*Primary Examiner*—Richard L. Raymond
*Attorney, Agent, or Firm*—Stroock & Stroock & Lavan LLP

[57] ABSTRACT

Methods and compositions for the prevention and/or inhibition of primary and secondary metastatic neoplasms are described. Individuals at a high risk of developing neoplasia and/or cancer patients undergoing conventional therapies may be treated with an effective dose of a salt of aminoimidazole carboxamide.

10 Claims, No Drawings

TREATMENT AND PREVENTION OF PRIMARY AND METASTATIC NEOPLASMS WITH SALTS OF AMINOIMIDAZOLE CARBOXAMIDE

1. INTRODUCTION

The present invention is directed to compositions and methods for the prevention and/or inhibition of primary and secondary metastatic neoplasms by treatment with salts of aminoimidazole carboxamide (AICA). Use of the entire group of organic acid salts and phosphates of 5-aminoimidazolecarboxamide rather than only those obtained from orotic acid are encompassed by the methods of the invention. For example, AICA may also be reacted with aliphatic acids such as lactic, succinic, maleic, citric, and tartaric or with sugar acids such as gluconic, galactonic, etc., particularly penta and poly, hydroxycarboxylic acids to form organic acid salts or AICA may be reacted with inorganic acids selected from hydrochloric and/or phosphoric acid to form inorganic salts, suitable for use according to the methods of the present invention. Inorganic salts thus formed would include hydrochlorides and/or phosphates. The method involves treating an individual at enhanced risk for cancer and/or suffering from cancer, with a therapeutically effective dose of a salt of aminoimidazole carboxamide. In the practice of the cancer treatment method of the invention, compositions containing AICA or a salt thereof are used to inhibit the proliferation of cancer cells at the primary and secondary sites and cells of the surrounding stromal tissues. Preferred compositions of the invention are those which specifically or preferentially prevent transformation of preneoplastic cells to tumor cells, and inhibit tumor cell proliferation, invasion and metastasis without general cytotoxic effects.

2. BACKGROUND OF THE INVENTION

AICA is referred to as "Orazamide" in the literature. Orazamide, a salt of aminoimidazole carboxamide (hereinafter referred "AICA"), has been used as a hepatoprotectant based on its ability to prevent necrosis and stimulate regeneration of the liver parenchymal cells.

2.1. Chemical Nature and Properties of Salts of Aminoimidazole Carboxamide

Orazamide is available in different forms as: 5-aminoimidazole-4-carboxamide orotate, 4-amino-5-imidazole carboxamide orotate or a combination of 1,2,3,6-tetrahydro-2,6-dioxo-4-pyrimidine carboxylic acid with 5-amino-1H-imidazole-4-carboxamide (1:1) or a combination of orotic acid with 5(or 4)-aminoimidazole-4(or 5)-carboxamide (1:1). The $C_5$ amine group on the imidazole ring can be attached to the $C_4$ carboxyl group of orotic acid or any other organic acid which is chemically compatible to the body:

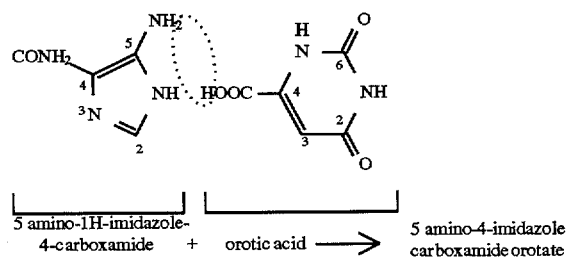

The known pharmacological activity of AICA orotate or orazamide resides in AICA and/or orotic acid. AICA is incorporated into animal nucleic acids, especially in purine biosynthesis. Orotic acid, also found in milk, is a pyrimidine precursor in animal organisms. Thus, AICA orotate contains precursors of purine and pyrimidine components of nucleic acids and its application as a hepatoprotectant was based on its stimulatory effects on regeneration of liver parenchymal cells.

2.2. Pharmacokinetics of AICA Salts

Orazamide or AICA orotate is currently used as a hepatoprotectant. AICA has been found to prevent liver necrosis and stimulate regeneration of the liver parenchymal cells. Upon administration of an AICA salt, AICA is the major metabolite.

2.3. AICA Salts and Cancer

The observation that AICA is utilized as a precursor in purine biosynthesis by normal and tumor cells suggested that an analog of AICA may exert an antitumor activity by inhibiting the biosynthetic pathway to nucleic acids. Hano, K., and Akashi, A., 1964, *Gann* 55:25–35. Therefore, a series of triazenoimidazoles, analogs of AICA in which the 5-amino group has been replaced by various monoalkyl- and dialkyltriazeno groups, have been synthesized and evaluated for antitumor activity. Shealy, Y. F., and Kranth, C. A., 1966, *J. Med. Chem.* 9:34–38, Shealy, Y. F., et al., 1962, *J. Org. Chem.* 27:2150–2154; and Shealy, Y. F., et al., 1961, *J. Org. Chem.* 26:2396–2401. One of these, 5-(dimethyltriazeno) imidazole-4-carboxamine (DTIC or DTIC-Dome, Dacarbazine), having the following formula:

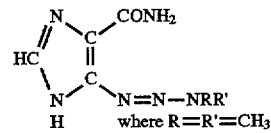

has exhibited notable activity against mouse sarcoma 180, adenocarcinoma 755, leukemia L1210 (Shealy, Y. F., et al., 1962, *Biochem. Pharmacol.* 11:674–676) and melanoma cells, (Rutty, C. J., et al., 1984, *Br. J. Cancer* 48:140).

Dacarbazine or DTIC-Dome is used as an anticancer agent in humans. After intravenous administration of DTIC-Dome, the volume of distribution exceeds total body water content suggesting localization in some body tissue, probably the liver. Its disappearance from the plasma is biphasic with an initial half-life of 19 minutes and a terminal half-life of 5 hours. The average cumulative excretion of unchanged DTIC in the urine is 40% of the injected dose in 6 hours. DTIC is subject to renal tubular secretion rather than glomerular filtration. At therapeutic concentrations DTIC is not appreciably bound to human plasma protein. DTIC is degraded extensively in man. Besides unchanged DTIC, 5-aminoimidazole-4-carboxamide (AICA) is the major metabolite of DTIC excreted in the urine. AICA is not derived endogenously, but from the injected DTIC, because the administration of radioactive DTIC labeled with $^{14}C$ in the imidazole portion of the molecule (DTIC-2-$^{14}C$) gives rise to AICA-2-$^{14}C$. Although the exact mechanism of action of DTIC-Dome is not known, three hypotheses have been offered: 1. Inhibition of DNA synthesis by acting as a purine analog; 2) action as an alkylating agent; and 3) interaction with SH groups. DTIC-Dome is indicated in the treatment of metastatic malignant melanoma. In addition, DTIC-Dome is also indicated for Hodgkin's disease as a secondary-line therapy when used in combination with other effective agents.

Even though AICA is the major metabolite of DTIC, there is no suggestion in the prior art nor any evidence to indicate whether the AICA formed is important in bringing about the anti-tumor and/or antimetastatic effect of DTIC-Dome. There is no prior art to suggest that DTIC-Dome may be a prodrug for AICA. The term "prodrug" as used herein describes pharmacologically inactive chemical derivatives of a drug molecule that require a transformation within the body in order to release the active drug. In fact, analogs of AICA such as DTIC-Dome were developed with the objective to block and/or compete with AICA and interfere with the synthesis of nucleic acids. In this regard, there is one report by Hakala et al., 1964, *Biochem. Biophys. Acts.* 80:666-668, indicating that AICA prevented the growth inhibitory effects of the chemotherapeutic agent, 6-mercaptopurine on tumor cells in vitro. However, in this connection, it has also been reported that AICA has been found to be able to prevent 6-mercaptopurine induced suppression of lymphocyte responsiveness in vitro. Al-Safi, S. A., and Maddocks, J. L., 1984, *Br. J. Clin. Pharmac.* 17:417-422. In addition, AICA was found to exhibit an antioxidant activity and increase the superoxide dismutase expression in lymphocytes incubated in vitro. Muzes, G., et al., 1990, *Acta Physiologica Hungarica* 76:183-190. Clearly, the use of AICA alone or in combination with a cancer chemotherapeutic agent has not been tested before in the prevention and treatment of primary and metastatic neoplastic diseases.

2.4. Cancer Growth and Chemotherapy

Cancer is a disease of inappropriate tissue accumulation. This derangement is most evident clinically when tumor tissue bulk compromises the function of vital organs. Contrary to what is generally thought, human malignant disorders are usually not diseases of rapid cell proliferation. In fact, the cells of most common cancers proliferate more slowly than many cells in normal tissues. It is a relatively slow accumulation of tumor tissue within vital organs that proves fatal to most patients who die of cancer.

Chemotherapeutic agents share one characteristic: they are usually more effective in killing or damaging malignant cells than normal cells. However, the fact that they do harm normal cells indicates their potential for toxicity. Understanding the use of chemotherapy requires a comprehension of both the drugs' mechanisms of action and the pathophysiology of cancer, which is rooted in deranged cellular and tissue growth.

Nearly all chemotherapeutic agents currently in use interfere with DNA synthesis, with the provision of precursors for DNA and RNA synthesis, or with mitosis. Such drugs are most effective against cycling cells. The mechanism of cell death after treatment with any single agent or combination of agents is complex and is likely to include more than one process. Because most clinically detectable tumors are composed mostly of noncycling cells, it is not surprising that chemotherapy is not always effective in eradicating cancer.

The strategy of cancer treatment is to shift tumor cells from a noncycling compartment to a cycling compartment. Several methods that promote this shift form the basis for combined-modality treatment. Surgery is most commonly used to reduce tumor size and thus facilitate reentry of cancer cells into the cell cycle. After a primary tumor is completely removed, microscopic metastases may remain at distant sites. Because of their small size, the micrometastases are composed principally of cycling cells. Small numbers of cells that remain at the primary tumor site are also likely to reenter the cell cycle. Thus, the remaining cancer cells are often susceptible to chemotherapy. Radiation therapy or chemotherapy alone can also be used to reduce tumor bulk and thus recruit cells into the cycling cell compartment. For example, the strategy of adjuvant chemotherapy for breast is based on these concepts. Weiss, R. B., and DeVita, Jr., V. T., 1979, *Ann. Intern. Med.* 91:251; Bonadonna, G., and Valagussa, P., 1988, *Semin. Surg. Oncol.* 4:250.

2.4.1. Combined Chemotherapy

Animal tumor investigations and human clinical trials have shown that drug combinations produce higher rates of objective response and longer survival than single agents. Frei, III, E., 1972, *Cancer Res.* 32:2593-2607. Combination drug therapy is, therefore, the basis for most chemotherapy employed at present. Combination chemotherapy uses the different mechanisms of action and cytotoxic potentials of multiple drugs. Although all chemotherapeutic drugs are most effective on cells that are synthesizing DNA, many agents—particularly the alkylating agents—can kill cells that are not cycling. Such agents are termed non-cell proliferation-dependent drugs. Some agents, including many of the antimetabolites and antibiotics, are most active against cells during DNA synthesis and are, therefore, termed cell-proliferation-dependent drugs. Repetitive administration of non-cell-proliferation-dependent agents can shrink tumor mass by killing cells in both the cycling and noncycling compartments of the tumor; the surviving cells will then move into the cycling compartment, where they are more susceptible to cell proliferation-dependent drugs. The combined use of agents less dependent on the cell cycle followed by those dependent on cell proliferation enhances tumor cell death. Each cycle of treatment kills a fixed fraction of cells, so repetitive cycles are required for cure. For example, a drug combination that kills 99.9 percent of cancer cells per treatment cycle would have to be repeated at least six times to eliminate an average tumor burden, if tumor cells did not regrow between cycles.

Several principles guide the selection of drugs to be used in combination. Drugs that are active individually are combined and administered in the highest doses the patient can tolerate and given as frequently as toxicity allows; drug combinations with limited overlaps of major toxicities are therefore preferable. The drugs selected should also have different mechanisms of action. This approach enhances cancer cell kill, reduces the chance that drug resistant cell populations will emerge, and disrupts cancer cell function by attacking multiple metabolic pathways. DeVita, V. T., et al., 1975, *Cancer*35:98. However, even though the chemotherapeutic agents are more effective in killing or damaging malignant cells than normal cells, the fact that they do harm normal cells indicates their great potential for toxicity. For chemotherapy to be effective, the patient must be in good physiologic condition.

2.4.2. Strategies in the Use of Chemotherapy

Cancer treatment requires inhibition of a variety of factors including tumor cell proliferation, metastatic dissemination of cancer cells to other parts of the body, invasion, tumor-induced neovascularization, and enhancement of host immunological responses and cytotoxity. Conventional cancer chemotherapeutic agents have often been selected on the basis of their cytotoxicity to tumor cells. However, some anticancer agents have adverse effects on the patient's immunological system. Unfortunately, for the vast majority of conventional antineoplastic agents the margin between an effective dose and a toxic dose, i.e., the therapeutic index, is extremely low. Thus, it would be greatly advantageous if a cancer therapy or treatment could be developed that would afford noncytotoxic protection against factors that might lead to growth, progression and metastasis of invasive cancers.

3. SUMMARY OF THE INVENTION

The present invention is directed to a method for the prevention and/or treatment of primary and metastatic neoplasms which involves using a salt of AICA to treat a patient suffering from a cancer. Accordingly, an effective dose of an AICA salt is administered to an individual suffering from a cancer. Cancers which may be responsive to growth inhibition by AICA include, but are not limited to, cancers of the colon, breast, prostate, brain, neuroblastomas, ovarian, lung, malignant gliomas, and other cancers of the gastrointestinal tract and head and neck region. The present invention is also directed to a method of evaluating susceptibility of a cancer to growth inhibition with an AICA salt.

The present invention is also directed to a method for the prevention and/or treatment of metastatic neoplasms which involves using an effective dose of an AICA salt along with conventional chemotherapy or hormonal and/or radiation therapy or surgery, to treat a patient suffering from cancer.

The present invention is also directed to a method for preventing immunosuppression induced by anticancer chemotherapeutic agents or for inducing immunostimulation in a patient suffering from cancer, which involves using an effective dose of an AICA salt.

The method of the invention relates to therapeutic protocols for treatment of cancer using salts of AICA and an acid including aliphatic acids such as lactic, succinic, maleic, citric, and tartaric or with sugar acids such as gluconic, galactonic, etc., particularly penta and poly, hydroxycarboxylic acids to form organic acid salts or AICA may be reacted with inorganic acids selected from hydrochloric and/or phosphoric acid to form inorganic salts. The method of the invention relates to therapeutic protocols for treatment of different types of cancer using AICA orotate as an adjuvant chemotherapeutic agent.

4. DETAILED DESCRIPTION OF THE INVENTION

The method of the invention involves administering an effective dose of an organic acid salt or inorganic acid salt of AICA to an individual who is identified as being at enhanced risk for cancer and/or as having cancer, in order to treat and prevent primary and/or metastatic cancer.

It will be apparent to those skilled in the art that other AICA-related compounds which inhibit cancer cell proliferation and spread may be useful as therapeutic agents. Such additional compounds may be identified using growth-inhibition assays described herein.

While the applicant is under no duty or obligation to explain the mechanism by which the invention works and certainly does not intend in any way for the invention to be limited to any particular mechanism of action, it may be that the ability of AICA salts to inhibit tumor cell proliferation, to inhibit the metastatic dissemination of tumor cells, to induce immunostimulation and/or to prevent immunosuppression induced by some chemotherapeutic agents used in cancer patients, contribute to the efficacy or effectiveness for use in the treatment and prevention of primary and secondary neoplasms. These proposed mechanisms of action are in no way meant to limit the scope of the invention and are presented purely for explanatory and/or illustrative purposes.

For example, the most life-threatening aspect of cancer is the uncontrolled growth and undetected spread of cancer cells throughout the body.

4.1. Pathobiology of Invasion and Metastasis

The two essential features of cancer are invasion and metastasis. At one extreme, microinvasion of the basement membrane characterizes the transition from neoplasia to cancer, and at the other extreme, metastases generally lead to death.

Invasion into the underlying connective tissue by the primary tumor proceeds in stages and is facilitated by various mediators produced by the tumor cells. Tumor cells that have not invaded the basement membrane and remain confined within the epithelium are termed carcinoma in situ. Release of collagenase IV by these cells dissolves the collagen in the basement membrane and allows the tumor to penetrate the subjacent stroma. Invasive tumor cells carry membrane receptors for laminin and fibronectin, large glycoprotein components of the basement membrane and connective tissue stroma, respectively. Binding to these elements provides the tumor cells with a lattice for anchorage and advancement. Enzymes released by tumor cells, such as plasminogen activators, collagenases I, II and III, cathepsins, heparanase and hyaluronidase, destroy matrix constituents, including fibrin, glycoproteins, proteoglycans and hyaluronic acid, thus enabling the cells to advance further into the connective tissue. Tumors also secrete inflammatory mediators such as prostaglandins, free radical oxidants and oxidative adducts, and autocrine motility factors, which direct the motion of the advancing tumor, vascular permeability factors which allow plasma proteins to accumulate in the tumor, and angiogenic factors which increase the vascularity of the tumor. Tumor cells preferentially invade along pathways that provide the least resistance, such as the connective tissue stroma. Tumors are much less likely to invade resistant tissue such as fascia, bone or thick-walled arteries and arterioles. However, they readily penetrate the venous capillaries or lymphatics, which have walls composed of a single layer of cells. Because the venous and lymphatic systems are interconnected, tumor cells that enter a lymphatic vessel may become enmeshed in a lymph node or may enter the venous circulation and disseminate to distant sites. As tumors enlarge, the intratumor vascularity may be compromised, thereby leading to hemorrhage and necrosis and a decrease in the growth fraction.

Metastases, on the other hand, may form when circulating tumor cells with adherent lymphocytes and platelets are trapped in capillaries and the tumor cell membrane interacts with the capillary endothelium. The capillary endothelial junctions retract, and tumor cell ligands bind to receptors on the endothelial and basement membranes. Tumor cells then release collagenase IV, which destroys collagen IV, a major component of the underlying basement membrane. Invasion of the subcapillary connective tissue is aided by binding to the glycoproteins laminin and fibronectin, by the release of proteases that destroy the matrix, and by the secretion of motility and chemotactic factors. Tumor cells then may proliferate and synthesize platelet aggregatory factors such as thromboxanes and procoagulants, thereby leading to the deposition of a fibrin cocoon around the cells. Such a cocoon may protect the micrometastasis from attack by the host's immune system.

Some experimental tumors in animals and most spontaneous human tumors are accompanied by increased concentrations of local and circulating prostaglandins, free radical oxidants, oxidative adducts, immunosuppression, bone metastasis, and hypercalcemia. Since prostaglandin E2 has immunosuppressive and osteolytic activities, PGE2 has been implicated in such paraneoplastic symptoms. Karmali, R. A., 1983, *CA Cancer J Clin.* 33:322–332. Some studies have implicated platelet aggregation and the effects of prostaglandins thereon in the hematogenous metastasis of tumors. There is evidence that platelets play an important role in metastatic dissemination of cancer cells. Tumor cells display specific properties towards platelets and the vascular endothelium. Platelet aggregation is induced by tumor cells, and aggregating platelets elaborate growth factors that promote tumorigenesis.

Since the aggregation of platelets requires production of lipid peroxides and/or thromboxane from arachidonic acid metabolism, improved understanding of how thromboxane $A_2$ inhibition is achieved can be expected to exert antimetastatic effects. Karmali et al., *Prost. Leuk. Essential & Fatty Acids* 48:309–314 (1993) reported that inhibition of thromboxane $A_2$ synthesis by eicosapentaenoic acid inhibited experimental metastasis of mammary adenocarcinoma cells in rats. Thromboxane $A_2$ synthesis can be inhibited by imidazole compounds, e.g., aminoimidazole carboxamide. Morrobin, D. F., et al., 1978, *Med. Hypothesis* 4:178–184; and Terao, S., et al., 1985, *Advances in Prostagl. Thromb. Leuk Res.* 15:315–315. In addition, AICA was found to have antioxidant activity and to increase superoxide dismutase activity. Muzes, G. et al., 1990, *Acta Physiologica Hungarica* 76:183–190.

Therefore, administration of AICA or a salt thereof, which are imidazole compounds, can result in inhibition of thromboxane $A_2$ and/or enhanced antioxidant defenses against oxidants and free radicals by superoxide dismutases. The net result is the inhibition of metastatic neoplasms in an individual suffering from cancer.

Pharmaceutical intervention directed to specific lymphocyte functions also offers a new approach to cancer treatment and prevention. For example, tumors are heterogenous tissues containing a supporting stroma that is infiltrated, to varying degrees, with lymphocytes. These tumor-infiltrating lymphocytes have been isolated, activated with interleukin-2 (IL-2) in vitro and used to treat patients with advanced cancers. However, treatment of patients with anti-cancer agents such as chemotherapeutic drugs or ionizing radiation can be very immunosuppressive. Several forms of toxic and drug-induced tissue damage involve free radical mechanisms. Gerson, R. J., et al., 1985, *Biochem. Biophys. Res. Commun.* 126:1129–1135. Lymphocytes are highly sensitive to destruction by many chemotherapeutic drugs and ionizing radiation. As expected, immunosuppression caused by these agents often leads to increased susceptibility to infection. In addition, many anti-cancer agents are immunosuppressive as well as mutagenic. Induction of a second malignancy may therefore follow successful therapy of the first cancer as a late complication of successful chemotherapy or radiation therapy. Harris, C. C., 1979, *J. Natl. Cancer Inst.* 63:275–277. Most second malignancies originate from the hematopoietic, lymphopoietic and reticuloendothelial systems, which are the most sensitive direct targets of the immunosuppressive anti-cancer agents. For example, some anticancer chemotherapeutic agents such as 6-mercaptopurine have been found to inhibit lymphocyte activity in vitro. It was also found that AICA has been able to prevent the 6-mercaptopurine induced inhibition of lymphocyte activity. Al-Safi, S. A., and Maddocks, J. L., 1984, *Br. J. Clin. Pharmac.* 17:417–422. Thus, administration of AICA along with 6-mercaptopurine can prevent the suppression of lymphocyte responsiveness in vivo. In addition, AICA was found to increase the activity of superoxide dismutases in lymphocytes, thereby providing an effective means to remove highly toxic free oxygen radicals which are often induced by toxic chemotherapeutic agents. Muzes, G., et al., 1990, *Acta Physiologica Hungarica* 76:183–190.

Along with other signals necessary for immune regulation, cytokines are likely to play a major role in the development of effective cancer immunotherapy. Therefore, AICA salts can be administered in combination with cytokines such as INF-$\alpha$, IFN-$\gamma$, TNF-$\alpha$, IL-2, IL-4, IL-6 and thymosin $\alpha$, to stimulate T cell activation in cancer patients for anti-tumor immunotherapy.

4.2. Choice of AICA Salt and Dosage

4.2.1. Active Chemical Structure

The present invention provides a number of different organic acid salts of aminoimidazole carboxamide which inhibit tumor cell proliferation and/or metastasis, e.g., 5-aminoimidazole-4-carboxamide orotate (AICA orotate) or 4-amino-5-imidazolecarboxamide orotate (AICA orotate) or a combination of 1,2,3,6-tetrahydro-2,6-dioxo-4-pyrimidine carboxylic acid compound with 5-amino-1H-imidazole-4-carboxamide (1:1) or a combination of orotic acid compound with 5(or 4)-aminoimidazole-4(or 5)-carboxamide (1:1); salts of AICA with aliphatic acids such as lactic, succinic, maleic, citric, and tartaric or with sugar acids such as gluconic, galactonic, etc., particularly penta and poly, hydroxycarboxylic acids to form organic acid salts; and inorganic acid salts such as hydrochlorides and/or phosphate salts of AICA suitable for use according to the methods of the present invention.

4.2.2. Formulation

AICA salts may be formulated into pharmaceutical preparations for administration to mammals for treatment of primary and metastatic neoplasms. AICA salts may be prepared, packaged, and labelled for treatment of an indicated tumor, such as a colon, breast, prostate, brain, neuroblastoma, ovarian, lung, glioma, tumors of the gastrointestinal tract or tumors of the head and neck region.

Many of the AICA compounds may be provided as organic acid salts with pharmaceutically compatible counterions, a form in which they are merely water-soluble. Pharmaceutically compatible salts may be formed with many acids, including, but not limited to, aliphatic acids such as lactic, succinic, maleic, citric and tartaric or with sugar acids such as gluconic, galactonic, etc., particularly penta and poly, hydroxycarboxylic acids and inorganic acids including, but not limited to hydrochloric and phosphoric acid. Salts tend to be more soluble in aqueous or other protonic solvents that are the corresponding free base forms.

The therapeutic compounds or pharmaceutical compositions may be administered intravenously, intraperitoneally, subcutaneously, intramuscularly, intrathecally, orally, rectally, topically, or by aerosol.

Patient dosages for oral administration range from 1–1000 mg/day, commonly 100–300 mg/day, and typically from 200–300 mg/day. Stated in terms of patient body weight, usual dosages range from 0.02 to 12.5 mg/kg/day, commonly from 1.25–3.75 mg/kg/day, typically from 2.5 to 3.75 mg/kg/day. Stated in terms of patient body surface areas, usual dosages range from 0.5–600 mg/m$^2$/day, commonly from 66–200 mg/m$^2$/day, typically from 130–200 mg/m$^2$/day.

Dosage amount and interval may be adjusted individually to provide plasma levels of the active moiety which are sufficient to maintain the anti-proliferative and anti-metastatic effects. Average plasma levels should be maintained with 10–100 microgram/ml, commonly from 10–50 microgram/ml, and typically from 10–20 microgram/ml.

Alternatively, one may administer the compound in a local, rather than oral manner, for example, via injection of the compound directly into a tumor, often in a depot or sustained release formulation.

A variety of delivery systems for the pharmacological compounds may be employed, including, but not limited to, liposomes and emulsions. The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Furthermore, one may administer the drug in a targeted drug delivery system, for example, in a liposome coated with tumor-specific antibody. The liposomes will be targeted to and taken up selectively by the tumor.

In cases of local administration or selective uptake, the effective local concentration of the drug may not be related to plasma concentration.

4.2.3. Evaluation of Anti-Proliferative Activity

According to the present invention, assays may be used to determine the susceptibility of particular cell lines to inhibition of proliferation by administering organic acid salts of AICA. Such assays are especially useful in evaluating whether a particular cancer may be treated successfully with an AICA salt. This method permits the choice of a therapeutic agent to be tailored to the biochemical characteristics of the individual tumor. The method may be practiced by growing the cancer cell line of interest in multiple sample plates or wells. Some sample plates contain varying concentrations of the AICA inhibitor so that an IC$_{50}$ may be calculated. The inhibitor-free plates serve as a control. The samples are cultivated for a time sufficient to allow measurable growth. The relative amount of growth in the presence and absence of the AICA compound is then determined. Cell growth may be measured by any number of methods, such as colony growth in soft agar or incorporation of $^3$H-thymidine. The cancer cell line to be evaluated may be obtained by biopsy of the individual human or animal patient.

Experimental tumor models may be used in pre-clinical experimental protocols to determine the susceptibility of particular metastatic and non-metastatic cancers in animals, to inhibition of proliferation and metastasis by administering salts of AICA.

4.3. Target Primary and Metastatic Cancers

Target cancers that are within the scope of the invention include those which comprise cancer cells at a primary site or those cancer cells established at a secondary metastatic site. Target cancers include, but are not limited to, cancers of the colon, breast, prostate, brain, neuroblastomas, ovarian, lung, malignant gliomas, and other cancers of the gastrointestinal tract and head and neck region. Cells of these cancers are responsive to the growth inhibitory effects of organic and inorganic acid salts of AICA.

The therapeutic methods of the invention are also directed at inhibiting the growth of non-malignant cells that support the growth and development of the primary neoplasm and/or metastatic lesions. Such non-malignant cells include vascular endothelial cells, other cells of the stroma and benign tumor cells. For example, a solid tumor's requirement for newly formed microvasculature may not be met by inhibiting the growth of vascular endothelial cells.

4.3.1. Prostate Cancer

One aspect of the invention relates to the treatment of prostate cancer. Prostate cancer is the second leading cause of death from cancer among men; 25 percent of men with prostate cancer die of the disease. Boring, C. C., et al., 1993, CA Cancer J. Clin. 43:7–26. Moreover, many patients who do not die of prostate cancer require treatment to ameliorate symptoms such as pain, bleeding, and urinary obstruction. Thus, prostate cancer is also a major cause of suffering and of health care expenditures. Catalona, W. J., 1994, New Eng. J. Med. 331:996–1004.

In making decisions about treatment for prostate cancer, clinicians consider the patient's age and general health, the clinical state and histological grade of the cancer, and factors concerning the quality of life, e.g., the immediate risks associated with treatment vs. the subsequent risks associated with advanced cancer. Cytotoxic chemotherapy is largely ineffective in treating prostate cancer. A combination of agents is no more effective than a single agent, and the addition of chemotherapy to hormonal therapy does not improve survival. Eisenberger, M. A., 1988, Chemotherapy for prostate carcinoma. In: Wittes, R. E., ed. *Consensus Development Conference on the Management of Clinically Localized Prostate Cancer.* NCI monographs No. 7 Washington D.C.: Government Printing Office: 151–153 (NIH publication no. 88-3005). Accordingly, there is a great demand for improved prostate cancer treatments.

The present invention provides a method of preclinical testing of AICA organic and inorganic salts in experimental prostatic cancer models, for example, in the androgen-independent Dunning R-3327-AT-I rat prostatic cancer model (Pinski, J., et al., 1994, Int. J. Cancer 59:51–55; the high metastatic potential prostatic cancer model PC-3-M (Koziowski, J. M., et al., 1984, Cancer Res. 44:3522–3529); and the non-metastatic DU-145 prostatic cancer model (Karmali, R. A., et al., Anticancer Res. 7:1173–1180). The present invention also provides a method of treating prostate cancers comprising administering a salt of AICA which prevents development of neoplastic cells, inhibits the proliferation and spread of cancer cells, stromal cells, and/or associated vascular endothelial cells and reduces the detrimental effects of toxicity caused by combination anti-cancer drugs.

5. TREATMENT AND PREVENTION REGIMENS FOR PRIMARY AND METASTATIC NEOPLASMS BY ADMINISTRATION OF AICA OROTATE

The invention is illustrated, by way of protocols for chemotherapy used in a patient suffering from cancer, which demonstrate the effectiveness of orazamide in the prevention and treatment of different cancers.

AICA orotate or other AICA salts may be used in combination with a variety of chemotherapeutic drugs which produce cytotoxicity by interfering with a variety of cellular processes. The compositions of the present invention are useful in preventing the transformation of preneoplastic cells to tumor cells, and inhibiting tumor cell proliferation, invasion and metastasis.

The commonly used chemotherapeutic agents which can be employed with the AICA salts according to the present invention include a variety of agents which are classified by their mode of action, origin or structure, although some drugs do not fit clearly into any single group. The categories include alkylating agents, antimetabolites, antibiotics, alkaloids and miscellaneous agents including hormones.

Alkylating agents (e.g., nitrogen mustard, cyclophosphamide, melphalan, busulfan, etc.) form covalent bonds with nucleic acids. These agents alter the integrity of DNA by transferring an alkyl group to the nucleic acids. Agents in this class have toxicities related to bone marrow depression, amenorrhea, male sterility, etc.

Antimetabolites (e.g., methotrexate, mercaptopurine, thioguanine, fluorouracil, etc.) are structurally similar to normal metabolic substrates. They impair cellular functions by substituting for normal precursors in vital physiologic reactions or by blocking these reactions. Agents in this class have toxicities related to bone marrow depression, liver damage, etc.

Antibiotics (e.g., doxorubicin, daunorubicin, bleomycin, etc.) are biologic products of bacteria and fungi. They do not share a single mechanism of action. For example, the anthracyclines, doxorubicin and daunorubicin achieve their cytotoxic effect by several mechanisms, including intercalation between DNA strands, production of free radicals, chelation of divalent cations and reaction with cell membranes. The wide range of potential sites of action may account for the broad efficacy as well as the toxicity of the anthracyclines. Myers, C. E., 1992, *Cancer Chemother. Biol. Response Modif.* 13:45.

Alkaloids (e.g., vincristine, vinblastine, vindesine, paclitaxel(taxol)) bind to the cytoplasmic structural protein tubulin and prevent the assembly or disassembly of microtubules. The neuropathy associated with the use of these drugs results from their action on microtubules in the long axons of nerves.

Miscellaneous agents have diverse actions. For example, dacarbazine and procarbazine (analogs of AICA) are similar in their modes of action to the alkylating agents. Asparaginase, on the other hand, acts enzymatically.

Hormones, particularly the steroid hormones (prednisone, progesterone, estrogen,) and androgen, are frequently used in cancer therapy. Other hormones that play important roles in cancer management include tamoxifen, an antiestrogen used to treat breast cancer, and leuprolide, a human gonadotropin-releasing hormone analogue, which is employed in the treatment of breast cancer and prostate cancer.

It is believed that the administration of an effective dose of a salt of AICA, e.g., AICA orotate, alone or in combination with one or more of one of the above-discussed chemotherapeutic agents may completely inhibit and prevent the growth and/or spread of a variety of primary and secondary cancers in vivo in patients. When another chemotherapeutic agent is administered together with an AICA salt, it is administered according to protocols and dosage ranges known to those skilled in the art suitable for such chemotherapeutic agent, The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

What is claimed is:

1. A method of inhibiting the growth of a cancer in an individual comprising administering to an individual in need thereof a therapeutically effective amount of a composition comprising a salt of 5-aminoimidazole-4-carboxamide.

2. The method according to claim 1 wherein the composition comprises 5-aminoimidazole-4-carboxamide orotate.

3. The method according to claim 1 wherein the composition comprises an organic acid salt derived from a combination of 5-aminoimidazole-4-carboxamide and an acid selected from the group consisting of orotic, lactic, succinic, maleic, citric, tartaric, gluconic and galactonic.

4. The method according to claim 1 wherein the composition comprises an inorganic acid salt derived from a combination of 5-aminoimidazole-4-carboxamide and an acid selected from the group consisting of hydrochloric and phosphoric.

5. The method according to claim 1 wherein the composition further comprises a cytokine selected from the group consisting of interferon-$\alpha$, interferon-$\gamma$, tumor-necrosis factor-$\alpha$, interleukin-2, interleukin-4, interleukin-6, and thymosin-$\alpha$.

6. A method of inhibiting metastatic spread of a cancer in an individual comprising administering to the individual a therapeutically effective amount of a composition comprising a salt of 5-aminoimidazole-4-carboxamide.

7. The method according to claim 5 wherein the composition comprises 5-aminoimidazole-4-carboxamide orotate.

8. The method according to claim 5 wherein the composition comprises a salt derived from the combination of 5-aminoimidazole-4-carboxamide with an organic acid selected from the group consisting of orotic, lactic, succinic, maleic, citric, tartaric, gluconic and galactonic.

9. The method according to claim 5 wherein the composition comprises an inorganic acid salt derived from a combination of 5-aminoimidazole-4-carboxamide and an acid selected from the group consisting of hydrochloric and phosphoric.

10. The method according to claim 5 wherein the composition further comprises a cytokine selected from the group consisting of interferon-$\alpha$, interferon-$\gamma$, tumor-necrosis factor-$\alpha$, interleukin-2, interleukin-4, interleukin-6 and thymosin-$\alpha$.

* * * * *